US011583228B2

(12) United States Patent
Jur et al.

(10) Patent No.: US 11,583,228 B2
(45) Date of Patent: Feb. 21, 2023

(54) FUNCTIONALIZED GARMENT AND USES THEREOF

(71) Applicant: North Carolina State University, Raleigh, NC (US)

(72) Inventors: Jesse S. Jur, Raleigh, NC (US); Amanda C. Myers, Raleigh, NC (US); Allison Bowles, Raleigh, NC (US); Raj Bhakta, Raleigh, NC (US); Braden M. Li, Raleigh, NC (US); Elizabeth Cobarrubias, Raleigh, NC (US); Michael Lim, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 436 days.

(21) Appl. No.: 16/784,297

(22) Filed: Feb. 7, 2020

(65) Prior Publication Data
US 2020/0253553 A1    Aug. 13, 2020

Related U.S. Application Data

(60) Provisional application No. 62/802,394, filed on Feb. 7, 2019.

(51) Int. Cl.
| | | |
|---|---|---|
| *H04W 12/33* | (2021.01) | |
| *A61B 5/00* | (2006.01) | |
| *G06F 1/16* | (2006.01) | |
| *A61B 5/24* | (2021.01) | |

(52) U.S. Cl.
CPC ......... *A61B 5/6805* (2013.01); *A61B 5/2415* (2021.01); *G06F 1/163* (2013.01)

(58) Field of Classification Search
CPC ..... A61B 5/6805; A61B 5/2415; A61B 5/318; A61B 5/6843; A61B 2562/164; A61B 2562/221; A61B 5/6823; A61B 5/6831; A61B 5/0008; A61B 2562/0215; A61B 5/0006; G06F 1/163; A41D 1/005; A41D 13/1281; H05K 1/038; H05K 2201/0281; H04W 12/33
See application file for complete search history.

(56) References Cited

U.S. PATENT DOCUMENTS

| | | | |
|---|---|---|---|
| 8,151,548 B1* | 4/2012 | Sherry | A01G 20/43 56/329 |
| 10,064,270 B2 | 8/2018 | Jur et al. | |
| 10,985,484 B1* | 4/2021 | Glickman | H05K 1/038 |
| 2012/0144551 A1* | 6/2012 | Guldalian | A61N 1/0484 2/102 |
| 2016/0338644 A1* | 11/2016 | Connor | A61B 5/1126 |
| 2017/0156662 A1* | 6/2017 | Goodall | A61B 5/7282 |
| 2018/0184735 A1* | 7/2018 | Longinotti-Buitoni | A61B 5/282 |
| 2018/0202874 A1* | 7/2018 | Ibrocevic | G01L 1/14 |
| 2019/0030411 A1* | 1/2019 | Yang | A41D 31/00 |
| 2019/0247650 A1* | 8/2019 | Tran | A61N 1/3704 |

* cited by examiner

*Primary Examiner* — Andrew Wendell
(74) *Attorney, Agent, or Firm* — Thomas | Horstemeyer, LLP

(57) ABSTRACT

Described herein are functionalized garments that can be worn on the torso of a subject and can be configured with varying zones or areas of compressions and can provide increased signal-to-noise ratios and reduced motion artifacts in areas while allowing a substantially unimpeded freedom of motion.

17 Claims, 5 Drawing Sheets

(Front)

(Front)          (Back)

FIG. 3 insulated, conductive thread is routed along panel seams

FUNCTIONALIZED GARMENT AND USES THEREOF

CROSS REFERENCE TO RELATED APPLICATIONS

This application claims priority upon U.S. provisional application Ser. No. 62/802,394, filed Feb. 7, 2019. This application is hereby incorporated by reference in its entirety.

STATEMENT REGARDING FEDERALLY SPONSORED RESEARCH

This invention was made with Government support 1160483 awarded by the National Science Foundation. The Government has certain rights in the invention.

BACKGROUND

Facile integration of electronics represent the most difficult challenge and greatest opportunity facing wearable technologies today, particularly for garment-based electronic designs. This can be addressed by applying macro-scale strategies for innovative materials design and manufacturing to solve the trade-off issues that exist between textile and device performance in the field of electronic textiles (e-textiles). Prior development has produced a garment made of multiple panels with individual properties and functionality. Assembling this garment, however, is challenging due to sewing multiple panel sections and integrating electrical components and connections.

SUMMARY

Described herein are functionalized garments that can be worn on the torso of a subject and can be configured with varying zones or areas of compressions and can provide increased signal-to-noise ratios and reduced motion artifacts in areas while allowing a substantially unimpeded freedom of motion.

The advantages of the invention will be set forth in part in the description which follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

Further aspects of the present disclosure will be readily appreciated upon review of the detailed description of its various embodiments, described below, when taken in conjunction with the accompanying drawings.

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are cited to disclose and describe the methods and/or materials in connection with which the publications are cited. All such publications and patents are herein incorporated by references as if each individual publication or patent were specifically and individually indicated to be incorporated by reference. Such incorporation by reference is expressly limited to the methods and/or materials described in the cited publications and patents and does not extend to any lexicographical definitions from the cited publications and patents. Any lexicographical definition in the publications and patents cited that is not also expressly repeated in the instant application should not be treated as such and should not be read as defining any terms appearing in the accompanying claims. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Where a range is expressed, a further aspect includes from the one particular value and/or to the other particular value. Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure. For example, where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In addition, the phrase "about 'x' to 'y'", where 'x' and 'y' are numerical values, includes "about 'x' to about 'y'".

It should be noted that ratios, concentrations, amounts, and other numerical data can be expressed herein in a range format. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it will be understood that the particular value forms a further aspect. For example, if the value "about 10" is disclosed, then "10" is also disclosed.

It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to 5%" should be interpreted to include not only the explicitly recited values of about 0.1% to about 5%, but also include individual values (e.g., about 1%, about 2%, about 3%, and about 4%) and the sub-ranges (e.g., about 0.5% to about 1.1%; about 5% to about 2.4%; about 0.5% to about 3.2%, and about 0.5% to about 4.4%, and other possible sub-ranges) within the indicated range.

As used in the specification and the appended claims, the singular forms "a," "an," and "the" include plural referents unless the context clearly dictates otherwise.

Throughout this specification, unless the context dictates otherwise, the word "comprise," or variations such as "comprises" or "comprising," will be understood to imply the inclusion of a stated element, integer, step, or group of elements, integers, or steps, but not the exclusion of any other element, integer, step, or group of elements, integers, or steps.

As used herein, a plurality of items, structural elements, compositional elements, and/or materials may be presented in a common list for convenience. However, these lists should be construed as though each member of the list is individually identified as a separate and unique member. Thus, no individual member of any such list should be construed as a de facto equivalent of any other member of the same list based solely on its presentation in a common group, without indications to the contrary.

As used herein, "about," "approximately," "substantially," and the like, when used in connection with a numerical variable, can generally refers to the value of the variable and to all values of the variable that are within the experimental error (e.g., within the 95% confidence interval for the mean) or within +/−10% of the indicated value, whichever is greater. As used herein, the terms "about," "approximate," "at or about," and "substantially" can mean that the amount or value in question can be the exact value or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

As used herein, "thermoplastic material" refers to a polymer that becomes pliable, moldable, and/or liquid above a threshold temperature and hard and/or solid when cold.

As used herein, "thermoset polymer" refers to a polymer based material made of monomers that polymerize (cure) when heated, subjected to a chemical reaction, or irradiated (e.g. exposure to UV light). Thermoset materials are typically liquid or malleable prior to curing.

As used herein, "conductive ink" refers to a material that can conduct electricity and can be molded into shapes and patterns and when set or dry results in an object or conduit.

Embodiments of the present disclosure will employ, unless otherwise indicated, techniques of textile engineering and manufacturing, electrical and computer engineering, computer science, physics and the like, which are within the skill of the art. Such techniques are explained fully in the literature.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible unless the context clearly dictates otherwise.

Discussion

Although many functionalized and "smart" garments exist, where sensors are involved, many suffer from poor signal acquisition because they do not have consistent or appropriate contact with the subject. As such, there exists a need for improved functionalized garments that can provide improved biopotential sensing.

With that said, described herein are functionalized garments that can be worn on the torso of a subject and can be configured with varying zones or areas of compressions that can provide increased signal-to-noise ratios and reduced motion artifacts in areas while allowing a substantially unimpeded freedom of motion. Other compositions, compounds, methods, features, and advantages of the present disclosure will be or become apparent to one having ordinary skill in the art upon examination of the following drawings, detailed description, and examples. It is intended that all such additional compositions, compounds, methods, features, and advantages be included within this description, and be within the scope of the present disclosure.

Figures 1A, 1B:
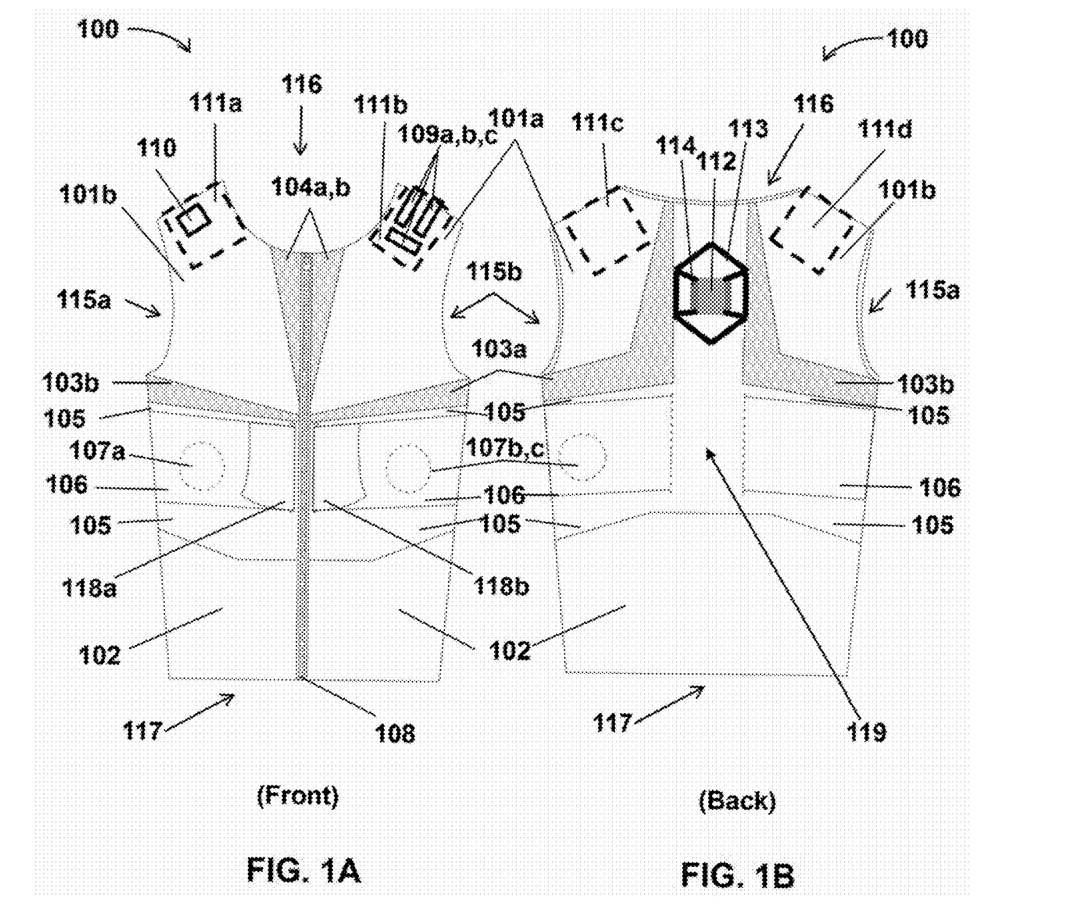
FIGS. 1A-1B show a front view (FIG. 1A) and a back view (FIG. 1B) of an embodiment of a functionalized garment as described herein.

With the general description of the functionalized garment in mind, attention is directed to FIGS. 1A and 1B provide an example of functionalized garment described herein, which show a front view (FIG. 1A) and a back view (FIG. 1B) of functionalized garment 100. The functionalized garment 100 can form a shirt, vest, or other type of garment configured to be worn on the torso of a subject, such as a human or other primate. The functionalized garment 100 can contain various zones or areas of compression, which can be attained by the use of varying types of textiles or fabrics that can have varying elastic moduli or stretch relative to each other. The functionalized garment 100 can be configured as a whole as a shirt (with or without sleeves) that does not contain a front opening. The functionalized garment 100 can be configured as a whole as a shirt (with or without sleeves) that opens completely in the middle of the front of the garment functionalized garment 100 via a fastener 108, such as a zipper, hook and loop fastener(s), buttons, snaps, or other suitable fastener. Embodiments with the opening in the front can have the advantage of being easier to put on a subject and/or can reduce the strain and wear and tear on the various sections, electronics, and other components of functionalized garment.

As shown in FIGS. 1A-1B, the functionalized garment 100 can have a first and second top panels (101a and 101b, respectively), where each panel extends to the front of the functionalized garment 100 to the back of the functionalized garment 100. These top panels can be made of a suitable fabric. Such suitable fabrics include, but are not limited to, any type of knit fabric. In some embodiments, the knit fabric can be a jersey knit. The term "Jersey" or "Jersey knit" fabric is a generally accepted term of art to describe a specific type of knit fabric and can include all types of jersey. The upper panels 101 a,b can be shaped so as to form at least part of left and right upper openings 116 a,b that can accommodate passage of an arm or other limb of a subject. One or both of the upper panels can include pockets 111 a,b that are on the inside of the functionalized garment that can be configured to contain one or more hard electrical components and/or connectors.

The functionalized garment 100 can further include a bottom panel 102. The bottom panel can extend from front to the back of the functionalized garment. In embodiments where the functionalized garment 100 is configured to open in the front, the bottom panel can be dissected into a front left and front right section that are continuous with the back section of the bottom panel 102. In embodiments where the functionalized garment is not configured to open in the front, then the bottom panel 102 is continuous around the bottom of the functionalized garment 102. The bottom panel 102 can be made of a suitable fabric. Such suitable fabrics include, but are not limited to, any type of knit fabric. In some embodiments, the knit fabric can be a jersey knit. The term "Jersey" or "Jersey knit" fabric is a generally accepted term of art to describe a specific type of knit fabric and can include all types of jersey. The bottom of the functionalized garment 100 can be configured to form a bottom opening 118 that can be extended through the central portion of the functionalized garment 100 such that it accommodates at least a torso of a subject, such as a human.

The functionalized garment 100 can include a first and a second front mesh insert 104 a,b. The front mesh inserts 104 a,b (collectively, 104) can be any suitable shape or dimension. In some embodiments where there functionalized garment does not contain a front opening, the first and the second front mesh inserts 104 a,b are continuous with each other such that they form a single front mesh insert. The front mesh insert(s) 104 can be tapered so as to be wider at the top (e.g. the part of the front mesh insert(s) 104 that forms part of a top opening of the functionalized garment) than at the bottom (e.g. the farthest point away from the top of the front mesh insert(s) 104). The front mesh insert(s) 104, can be made of any suitable mesh fabric or textile. The term "mesh" is a term of art that is generally known to refer to a loosely woven or knitted fabric such that it has a large number of closely spaced holes. Suitable meshes for the front mesh insert(s) can be made of any suitable fiber type including, but not limited to, cotton, polyester, nylon, rayon, blended fibers that include spandex, etc. The length of each of the front mesh inserts 104 can be about ⅓ of the total length of the functionalized garment 100. In embodiments where the functionalized garment is configured to open in the front, the width of each of the front mesh inserts at its widest point 104 a,b can range from about 2-10 cm. In embodiments where the functionalized garment is not configured to open in the front, the width of each of the front mesh insert 104 at its widest point can range from about 10-20 cm. The front mesh insert(s) 104 can be attached to one or both of the upper panels 101a,b. Together with the upper panels 101a,b, the front mesh insert(s) 104 can form at least the front portion of an upper opening 117. The upper opening 117 can be curved, elliptical, and/or circular to accommodate passage of a head and/or neck of a subject when worn by a subject.

The functionalized garment 100 can further include a continuous (in embodiments where the front of the functionalized garment 100 does not open) or discontinuous (in embodiments where the front of the functionalized garment 100 is configured to open) mesh panels 103 a,b (collectively or where continuous, 103). In embodiments configured to open in the front, the mesh panels can extend laterally from the fastener 108 across the upper edge of about the middle third of each side of the front of the functionalized garment 100, continue around the sides of the functionalized garment 100, and continue laterally across a portion of the back of the functionalized garment 100 that is less than halfway across the back portion of the functionalized garment 100. At this point, the mesh panels on both sides extend up the back of the functionalized garment 100 to the top opening 117 of the functionalized garment 100. As is shown in FIG. 1B, the mesh panels 103 a,b do not touch each other in the back of the functionalized garment 100. As discussed in greater detail below, the mesh panels are attached to and separated from each other at least in the back of the functionalized garment by a compression panel 105. It will be appreciated that where the mesh panels 103 a,b are continuous in the front, they form a single mesh panel. In these embodiments, the mesh panel 103 is not configured differently with respect to the back and the sides of the functionalized garment 100 relative to the embodiments that include the front opening and discontinuous mesh panels 103 a,b. However, as discussed above, the continuous mesh panel 103 differs from the discontinuous mesh panels 103 a,b in that the continuous mesh panel 103 is continuous across the front of the functionalized garment instead of being separated by a fastener 108.

The mesh panel(s) 103 can be made of any suitable mesh fabric or textile. The term "mesh" is a term of art that is generally known to refer to a loosely woven or knitted fabric such that it has a large number of closely spaced holes. Suitable meshes for the front mesh insert(s) can be made of any suitable fiber type including, but not limited to, cotton, polyester, nylon, rayon, etc. The width of the mesh panel(s) 103 can vary in width along their length. The width when measured at any given point along the length of the mesh panels can range from about 1 cm to about 10 cm.

The functionalized garment 100 can include a compression panel 105. The compression panel can extend from the top opening 116 on the back of the functionalized garment 100 down the middle region of the back of the functionalized garment 100 between the mesh panel(s) 103 in the upper region of the back of the functionalized garment 100 down to the bottom of about the middle third of the functionalized garment 100. The compression panel 105 can extend laterally on both sides of the middle portion of the compression panel 105 along the back side of the functionalized garment 100 and continue along the sides and laterally along the front of the functionalized garment 100. In embodiments that have a front opening, the compression panel 105 can end on the right and the left side of the front of the functionalized garment 100 where the right and left ends contact the fastener 108. In embodiments that do not have a front opening, the compression panel 105 is continuous as it extends laterally along the front side of the functionalized garment 100 in the middle third region of the functionalized garment 100. On the back of the functionalized garment 100, the portion of the compression panel 105 where the vertical middle portion and the lateral portion meet the compression panel can include a sleeve 119 that can be configured to receive an adjustable compression band 106. The sleeve can maintain the positioning of the adjustable compression band. The adjustable compression band can be coupled to the compression panel such that it can freely slide laterally through the sleeve and can be detachable from the functionalized garment 100. In some embodiments, the adjustable compression band 106 can be releasably or permanently attached to the functionalized garment 100 at one or more points along the compression panel 105. The compression panel 105 can be made of any suitable fabric or textile. The width of the compression panel 105 can vary along its length in the lateral or the vertical direction. It will be appreciated that where the compression panel 105 extends laterally, its length for this portion extends laterally and where the compression panel extends vertically along the back middle portion of the functionalized garment 100, the length can be considered to extend along the vertical axis of the compression panel 105. The width of the compression panel when measured at any one point along its length can range from about 10 cm to about 30 cm.

The compression panel 105 can be configured to conform to anatomical portions of the subject such as the abdomen and gluteal regions. As shown in FIG. 1A, the compression panel 105 can be wider towards the front-middle region of the functionalized garment 100 to provide abdominal support. As show in FIG. 1B the compression panel 105 can be wider towards the sides of the garment that can provide freedom of movement of the hips and sacral/gluteal region of the subject.

As discussed above, the functionalized garment can further include an adjustable compression band 106. The adjustable compression band 106 can form a belt extending laterally around the middle portion of the functionalized garment from back to front. The adjustable compression band 106 can be composed of an elastic material, fabric, or textile. In some embodiments, the adjustable compression band can be composed of or include spandex/lycra. In these embodiments, the amount of spandex/lycra can be greater that what is in other fabrics used in other regions of the functionalized garment. For example, the fabric in one or more other regions of the functionalized garment described herein can be, in some embodiments, can be about 80/20 polyester/spandex while in the adjustable compression band 106 can be about 73/27 polyester/spandex. The adjustable compression band 106 can have two ends 118 a,b (collectively 118) that can be coupled together in the front. The ends 118 can contain fasteners to hold the ends in place after adjustment. The fasteners can be hook and loop closures, snaps, buckles, or any other suitable device that can hold the ends in place after adjusting to maintain the desired level of compression during use. During use the adjustable compression band can be adjusted to increase the compression provided to the user by pulling on the ends 118 of the compression band 106. The compression band 106 can be a uniform width along its length. The compression band 106 can be varied in width along its length. The width of the compression band 106 when measured at any point along its length can range from about 10 cm to about 30 cm.

The functionalized garment 100 can include a bottom portion 102. The bottom portion 102 can be attached to the compression panel 105 and can form the bottom of the functionalized garment 100. The bottom portion 102 can form a bottom opening 117. In embodiments that have a front opening that extends the length of the front of the functionalized garment 100, it will be appreciated that the bottom opening 117 is only formed when the functionalized garment 100 is in the closed position. The bottom portion 102 can be made of a suitable fabric. Such suitable fabrics include, but are not limited to, any type of knit fabric. In some embodiments, the knit fabric can be a jersey knit. The term "Jersey" or "Jersey knit" fabric is a generally accepted term of art to describe a specific type of knit fabric and can include all types of jersey.

The functionalized garment 100 can contain one or more electrodes, sensors, interconnects, and/or other detection or connection devices (e.g. 107 a,b (collectively 107), FIGS. 1A-1B) that can detect and/or measure a biopotential of a subject. As used herein the term "biopotential" can refer to a biological signal or characteristic, including, but not limited to temperature, heart rate, blood oxygenation level, Electrocardiography (ECG) Electrodermal Activity (EDA) Electrogastrography (EGG) Electromyography (EMG).

The one or more electrodes, sensors, interconnects, and/or other detection or connection devices 107 can be coupled to the functionalized garment 100 in any desired location. The one or more electrodes, sensors, interconnects, and/or other detection or connection devices 107 can be flexible. In some embodiments, the one or more electrodes, sensors, interconnects, and/or other detection or connection devices 107 can be coupled to the inside of the functionalized garment 100 to allow for direct contact with a user. The one or more electrodes, sensors, interconnects, and/or other detection or connection devices 107 can be coupled to the compression panel 105. When in this location, as compression is applied by the adjusting the compression band 106, this can increase the security of the contact and position of the one or more electrodes, sensors, interconnects, and/or other detection or connection devices relative to a subject during use.

The one or more electrodes, sensors, interconnects, and/or other detection or connection devices 107 described herein can be printed using a suitable technique (e.g. screen-printed, direct-write printed, inkjet printed, etc.) onto an interface film that can be heat-laminated (thermoplastic polyurethane BEMIS ST644) onto the fabric and/or directly printed onto the fabric. The one or more electrodes, sensors, interconnects, and/or other detection or connection devices 107 can be made from a suitable conductive sensing material. Suitable conductive sensing materials can include, but are not limited to Ag/AgCl, Ag, carbon or any other conductive material that can be flexibly configured for integration into a textile or fabric. Ag/AgCl has a desirable cell potential for biopotential sensing. Conductive films on a film can be used to generate one or more of the electrodes, sensors, interconnects, and/or other detection or connection devices 107 described herein. Conductive films on a film such as TPU (thermoplastic polyurethane ST644) can range on the order of 10s of micrometers and can be directly printed on a textile can range from 100s of micrometers depending on penetration of conductive material into fiber bulk. The thickness of the conductive material can be about 20 to about 60 micrometers. When it is directly printed on a textile or fabric the thickness of the conductive film printed onto a textile can be about 60 to about 200 micrometers.

The functionalized garment 100 can include various hard electronic components, interfaces, and/or connectors. The hard electronic component(s) can be configured to receive, transmit, and/or store data collected from the one or more electrodes, sensors, interconnects, and/or other detection or connection devices 107. The hard electronic component(s) can be configured to provide heating and/or cooling to the subject. The hard electronic components can include, but are not limited to receivers, transmitters, memory storage, LEDs or other lighting sources, wires, traces, thermoelectric generators, processors. Where appropriate, the hard electronic component(s) can be configured to receive and/or transmit in radio frequencies and/or in any protocol such as Bluetooth protocol, WiFi, etc. The hard electronic component(s) can be a data acquisition device. The various hard electronic component(s) can be coupled (physically, electrically, or wirelessly) or be in communication with to one or more of the hard electronic component(s) and/or the one or more electrodes, sensors, interconnects, and/or other detection or connection devices 107 described elsewhere herein. The various hard electronic component(s) can be coupled to (physically, electrically, or wirelessly) or be in communication with other electrical components, computers, or any mobile device (such as a smart phone or tablet). One or more of hard electronic component(s) can be removably coupled to the functionalized garment 100.

As shown in FIGS. 1A and 1B, in some embodiments, the functionalized garment 100 can include an antenna 110 that can be configured to transmit and/or receive a signal. The functionalized garment 100 can include on or more TEGs (109a, b, c). The functionalized garment 100, in some embodiments, can include one or more printed circuit boards. The functionalized garment 100 can include a radio board 112, aSoC board, 114, and a printed circuit board case that can house the SoC board and/or the Radio board, which can be removably coupled to the compression panel 105 on the back of the functionalized garment 100 in the upper portion of the compression panel. One or more TEGs 109 can be incorporated and can be configured to heat or cool.

During use the one or more electrodes, sensors, interconnects, and/or other detection or connection devices 107 can detect and/or measure a biopotential from a subject. The one or more electrodes, sensors, interconnects, and/or other detection or connection devices 107 can produce a signal that can be transmitted to one or more of the hard electronic component(s), which can be configured to receive, process, store, and/or transmit the data contained in the signal to one or more one or more of the electrodes, sensors, interconnects, and/or other detection or connection devices 107, one or more of the hard electronic component(s), and/or one or more devices not contained in the functionalized garment 100, such as a computers, other processing device, and/or any mobile device (such as a smart phone or tablet). Data generated can be stored in memory contained on the functionalized garment 100, on memory external to the functionalized garment 100. The memory external to the functionalized garment 100 can be stand-alone memory (e.g. a flash drive or external hard drive), memory contained in a computer or mobile device, or be contained on a remote server such as those that make up the cloud.

When considering the mesh panel(s) 103 and mesh insert(s) 104 with respect to the upper panels 101 and compression panel 105, the collective positioning of the mesh panels 103 and mesh inserts 104 in the functionalized garment 100 are in areas of large bodily movement (e.g. around the shoulders). The inclusion of mesh in these specific locations can facilitate absorption of most of the motion induced by the arms and/or shoulder as they move during subject activity. This can reduce the translation of large bodily motion to the panels that contain the sensors and can facilitate reduction of motion artifacts and increase the signal-to-noise ratio of the sensors that are included in the functionalized garment. This can increase the sensitivity of the sensors in the functionalized garment 100 and can yield improved performance of the functionalized garment 100.

The skin-to-electrode (or other sensor or detecting device) can be modulated inter alia (either increased or decreased) by changing the conductive material, design of the electrode and/or sensor, and/or enhancement of interface by decreasing impedance through applying a topical (e.g. a lotion, hydrogel) to the skin of a user or via natural sweat build-up from skin of a user.

In certain aspects, conductive seams can be used to produce the garments described herein. Facile integration of electronics within garments is a challenge and opportunity facing wearable technologies, particularly for garment-based electronic designs. In this aspect, conductive seams implemented in the functionalized garments described herein can be used as wiring pathways for electronics. The conductive seams can be structured to produce a seam skeleton throughout the garment, which is also referred to herein as a wiring harness. The conductive seam contains predetermined wiring pathways and connection points for electronics. This allows for a plug-n-play ideology where the specific function of an individual panel (e.g., temperature or accelerometer sensing) can be exchanged to provide a different function (e.g., energy harvesting). Panels are attached to the conductive seams during the garment assembly process, which then connects and routes electronics for each panel to a common circuit board. The conductive seam can be localized to a specific panel in the garment or, in the alternative, the conductive seam can be integrated throughout the garment to produce a seam skeleton.

Referring to FIG. 1A, the first panel 101a can be attached to the first mesh insert 103a by a conductive seam. In another aspect, the first panel 101a can be attached to the fastener 104a by a conductive seam. In another aspect, the first panel 101a can be attached to the first mesh insert 103a and fastener 104a by a conductive seam. The same approach can be taken with the second panel 101b, where the second panel can be attached to the second mesh insert 103b and/or fastener 104b by a conductive seam.

Figure 2:
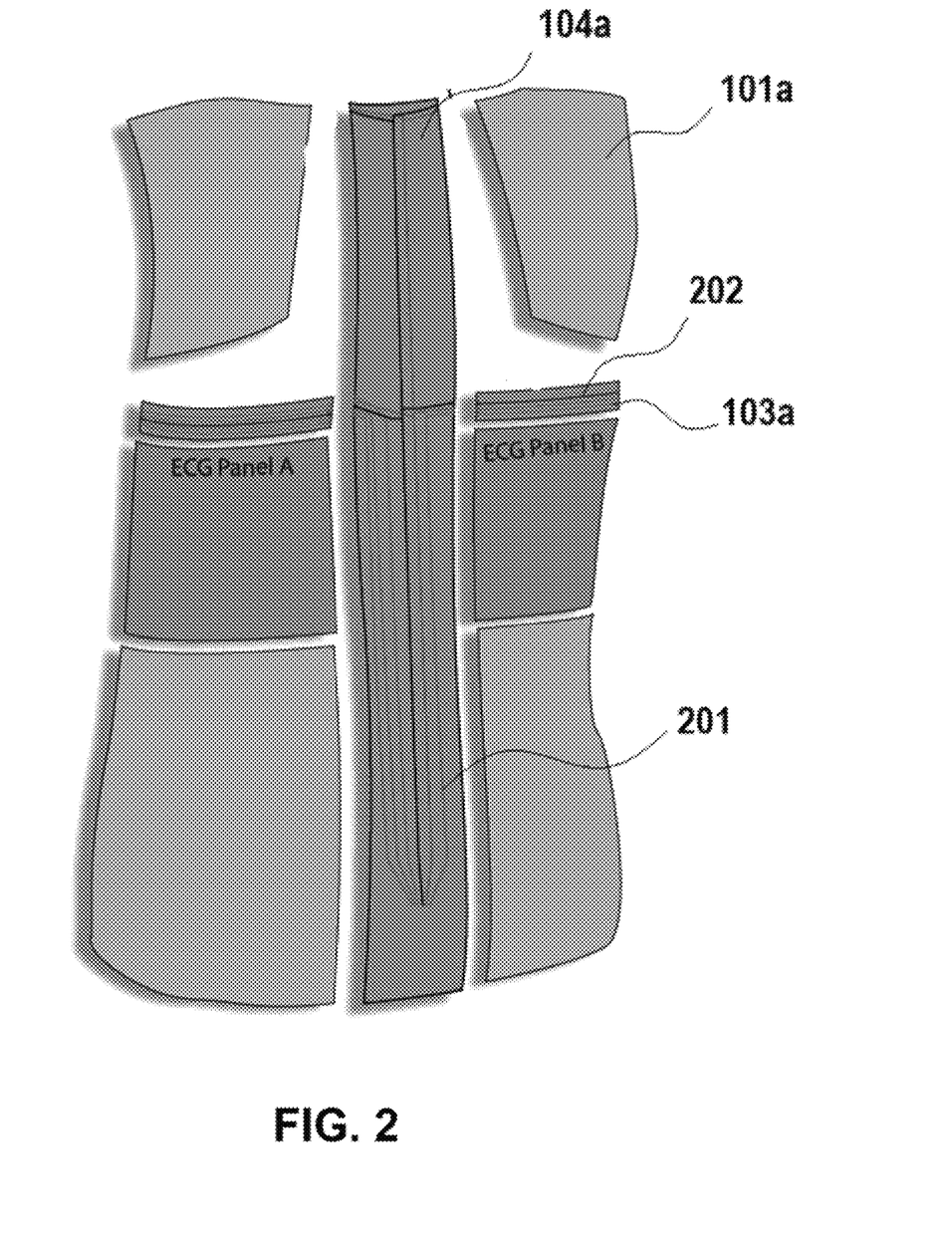
FIG. 2 shows an exploded view of the functionalize garment with seam skeleton.

Depending upon the application of the garment and the location of hard electronic components, the location of the conductive seam in the garment can vary. For example, when the first panel 101a is attached to the first mesh insert 103a by a conductive seam, the conductive seam can be used to entirely attach the first panel to the first mesh inset or, in the alternative, the first panel can be attached to the first mesh inset with a combination of conductive and non-conductive seams. FIG. 2 shows an exploded view of the functionalized garment with conductive seams 201 present in the fastener 104a and conductive seams 202 in the first mesh inset 103a The conductive seam provides a conduit for electrical information and data. In one aspect, the conductive seam comprises a connection point for the hard electronic component. Here information obtained from the hard electronic component via the one or more flexible sensors, flexible electrodes, and/or flexible interconnects is transmitted through the conductive seam. From the panel, the conductive seam provides a continuous conduit to any desired location in the garment. The conductive seam downstream can include a connection point to a circuit board, radio board, or antenna, where information produced from the hard electronic component in the panel can be further transmitted and/or processed.

Figure 3:
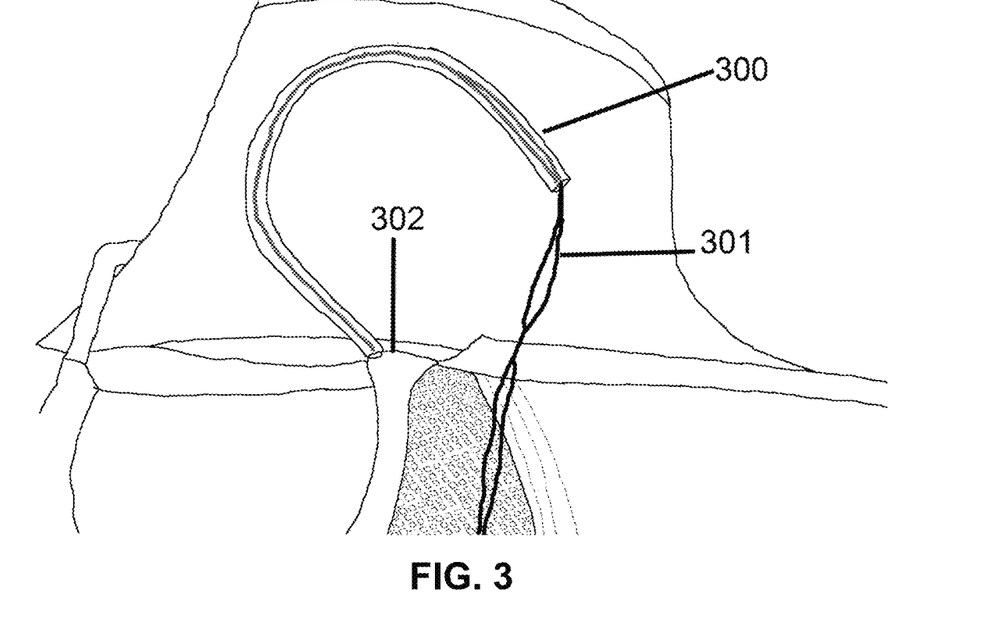
FIG. 3 shows one aspect of a conductive seam.

The conductive seam can take on several forms. In one aspect, the conductive seam comprises a fabric shaped as hollow tube for housing one or more wires. An example of this aspect is provided in FIG. 3. In this aspect, a pipe 300 housing wires 301 can be fed through the fabric seam 302. In another aspect, the wires are fed directly into the fabric seam without the use of the pipe.

Figure 4:
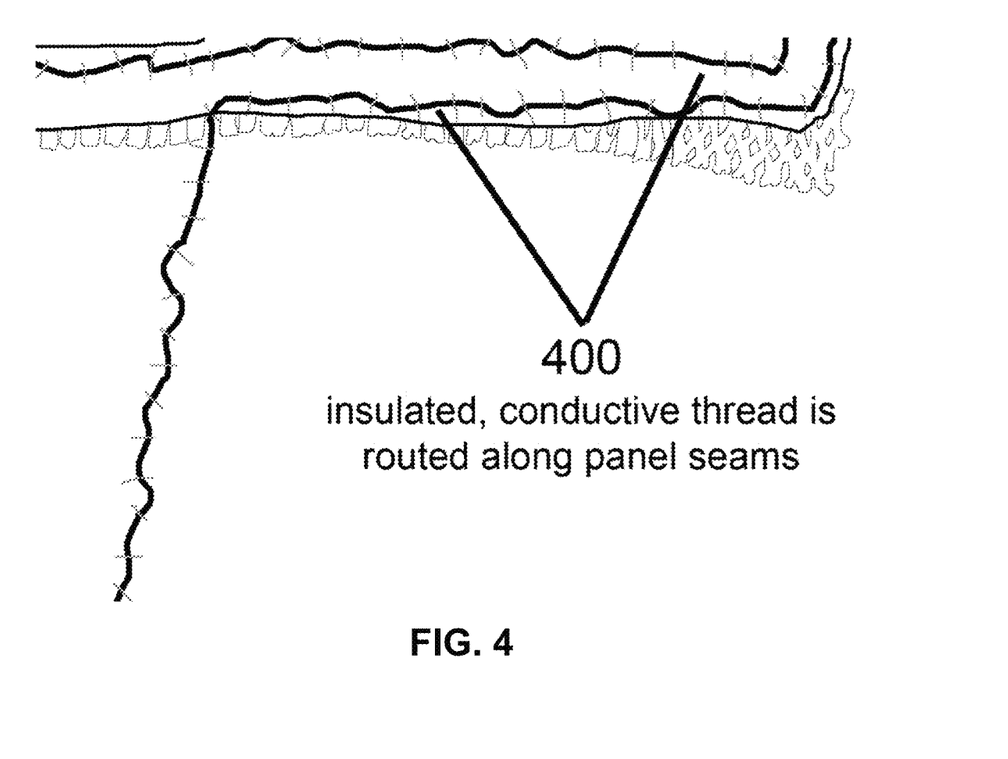
FIG. 4 shows the use of a conductive thread as a conductive seam.

In another aspect, the conductive seam comprises conductive yarn or threads. Referring to FIG. 4, conductive threads 400 are sewn along the seam. In one aspect, the smart yarns sold under the tradename Apache sold by Volt Premium Smart Yarns can be used herein.

In another aspect, the conductive seam is composed of a thin-film, fabric, or bias tape with patterned ink-based interconnects. The interconnects can be patterned by screen-printing, inkjet printing, direct write printing, or by spray coating over a mask. The techniques for printing ink-based interconnects disclosed in U.S. Pat. No. 10,064,270 can be used herein. The thin-film, fabric, or bias tape can be any shape, length, or size that is appropriate for forming the conductive seam in the garments described herein. Depending upon the material used to produce the conductive seam, a number of techniques can be used to secure the conductive seam to the panels. In one aspect, an adhesive can be used to secure the thin-film, fabric, or bias tape with patterned ink-based interconnects to the panel. In one aspect, thin-film, fabric, or bias tape with patterned ink-based interconnects can have an adhesive on each face, which can adhere to the panel and another substrate (e.g., mesh insert).

Figure 5A:
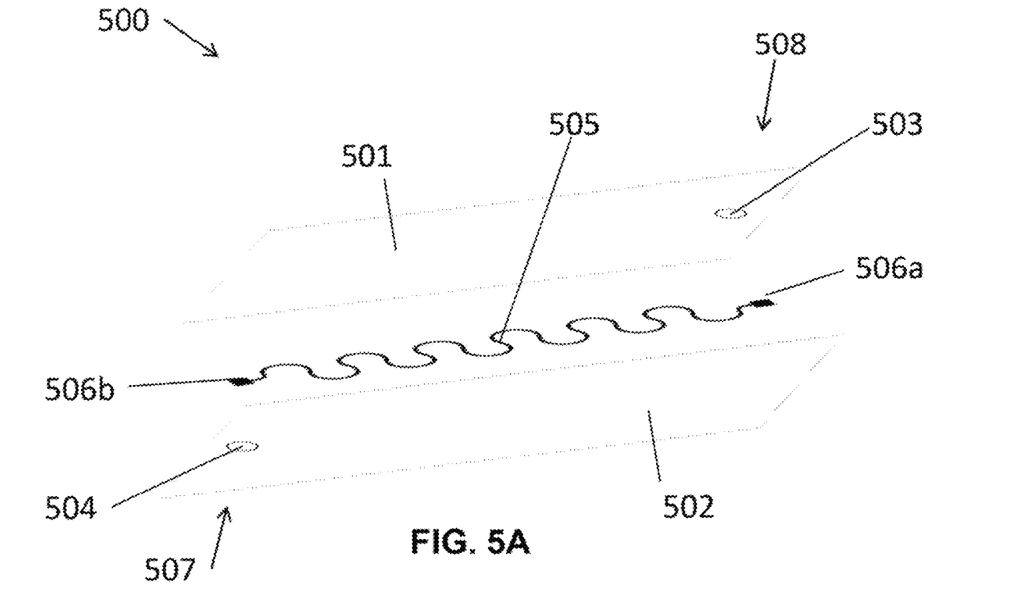
FIGS. 5A-5B show views of a flexible interconnect for use as a conductive seam.
Figure 5B:
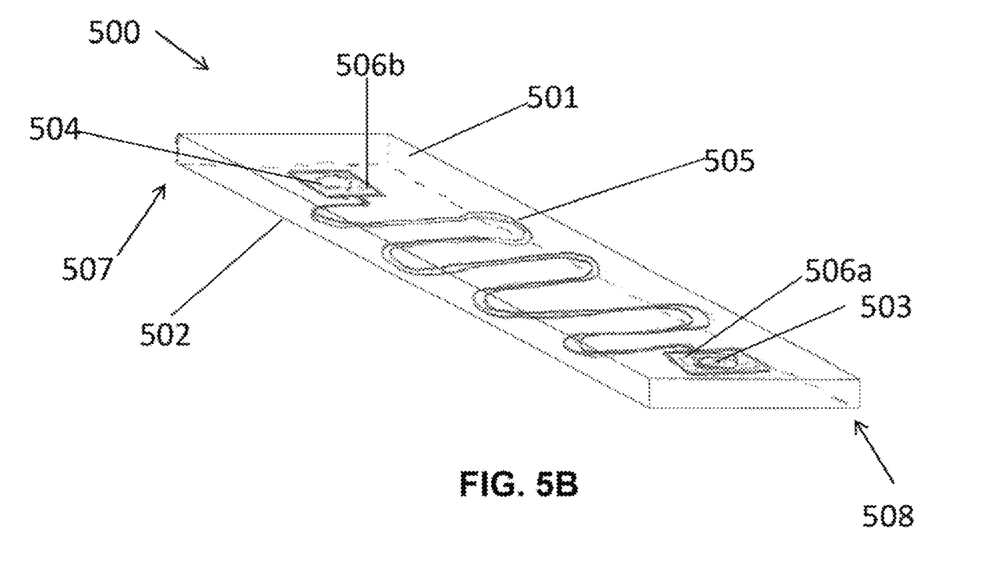

In another aspect, the conductive seam is composed of flexible interconnects that contain a conductive trace that can be encapsulated between two or more thermoplastic polymer films. FIG. 5A shows an exploded view of the flexible interconnect, while FIG. 5B shows the assembled flexible interconnect. In some aspects, all the individual components of the flexible interconnect are flexible. The flexible interconnect 500 can have a first thermoplastic polymer film 501 that forms the top layer of the flexible interconnect. The first thermoplastic polymer film 501 can have a first hole 503. The flexible interconnect 500 can have a second thermoplastic polymer film 502 that forms the bottom layer of the flexible interconnect 500. The second thermoplastic polymer film 502 can have a second hole 504. The first and the second thermoplastic polymer films can be made from any suitable thermoplastic polymer. Suitable thermoplastic polymers include, without limitation, polyurethane, polyethylene, vinylester, epoxys, polyamides, polypropylene, polyethylene terephthalate, polybutylene terephthalate, polyetherimide, polyvinylidene fluoride, polyetheretherketone, poly(acrylonitrile butadiene styrene) (ABS), polylactic acid (PLA), polycarbonate, polyvinyl chloride silicones, and any permissible combinations or copolymers thereof. In some aspects, the thermoplastic polymer film can be a composite material that can include any of the suitable thermoplastic polymer materials previously listed and one or more suitable filler material. Suitable filler materials can include organic and inorganic materials, such as, but not limited to, carbon nanotubes (CNTs), metal particles (e.g. Ag particles), graphene, nanowires (e.g. Ag nanowires), cellulose and the like.

The flexible interconnect 500 can have a conductive trace 505. The conductive trace can be made from any suitable conductive ink. Suitable conductive inks include, without limitation, silver, carbon, silver chloride, silver/silver chloride, gold, and combinations thereof. Other suitable conductive inks include, without limitation, dielectric inks, silver plated copper inks, and positive temperature coefficient inks. The conductive trace can be configured in or contain any shape or design (e.g., without limitation, curved lines, straight lines, zig-zag, sinusoid, horseshoe, and combinations thereof) that falls within the design parameters. The total length of the conductive trace can be any suitable length desired and will depend on inter alia, the application of the conductive seam in the garments described herein. In some embodiments the total length of the conductive trace can range from about 1 mm to about 300 mm. In other embodiments, the total length of the conductive trace can be greater than 300 mm.

The conductive trace can have a conductive pad electrically coupled to each end 506a, 506b (collectively 506). In some embodiments, the conductive pads 506 are integrated extensions of the conductive trace 505. In other words, the conductive pads 506 can be made of the same conductive ink and are seamless extensions of the conductive trace 505.

The flexible interconnect can be configured such that the conductive pads 506 are aligned with and in physical contact with the first hole 503 and the second hole 504 present in the first thermoplastic polymer film 501 and the second thermoplastic polymer film 502, respectively. Thus, the conductive pads 506 can be exposed through the first and the second thermoplastic polymer films 501, 502. In some embodiments, during manufacture of the flexible interconnect 500, the conductive ink that can be used to form the conductive trace 505 and/or conductive pads 506 can fill the holes 503, 504. In any instance, the exposed conductive pads 506 can facilitate an electronic via between two or more flexible interconnects 500 and/or a flexible interconnect 500 and an electrical component.

As shown in FIGS. 5A-5B, in some aspects, the holes 503, 504 can be placed at one end of the first and the second thermoplastic polymer film 501, 502, respectively, where when the flexible interconnect is assembled the holes 503, 504 are at opposite ends from one another. In these aspects, when the conductive pads 506 are aligned with the holes, each side of the flexible interconnect 500 has an exposed conductive pad. In this aspect, a flexible interconnect 500 with a "plus" end (e.g. 507) and a "minus" end (e.g. 508) can be manufactured.

The conductive trace 505 and conductive pads 506 (except for any exposed surface of the conductive pads 506 are encapsulated between the first and the second thermoplastic polymer film 501, 502.

In one aspect, the flexible interconnect that contains a conductive trace encapsulated between two or more thermoplastic polymer films can be placed between two substrates (e.g., panel and mesh insert), and the garment can be placed in a heat pressing machine in order to secure the flexible interconnect to the garment.

The conductive seam provides standard connection locations for each of the panels, which permits interchangeability between panels, as well as a standard connection methods. In one aspect, an electronic connection between the panels and conductive seam can be created by using metal snaps or metallized Velcro. This aspect does not create a permanent connection and can add additional, post-assembly, modularity to the garment. In another aspect, low temperature solder paste or other conducting epoxies can be applied to connection points on the conductive seam and the panels. Connections are then made by applying heat to melt the paste and electrically connect the panel to the conductive seam. In other aspects, thermal welding may be used to create an electrical connection between the conductive seam and panel in the garment. In other aspects, sonic welding can be used to electrically connect the panel to the conductive seam. When coupled to or otherwise integrated with the conductive seam provided herein, the electrical component(s) can have any number of connection points to the conductive seam as practically implementable.

The functionalized garments described herein can have a durability of about 20 to 50, 60, 70, 80, 90, 100 or more washes without a decrease in signal quality. Durability can be modified by varying, inter alia, the encapsulation of the one or more of the electrodes, sensors, interconnects, and/or other detection or connection devices 107. One or more of the hard electrical component(s) can be removed prior to washing.

Aspect 1: A functionalized garment configured to encompass the torso of a subject, the functionalized garment comprising:

an upper opening configured to allow the passage of the head and neck of a the subject a bottom opening, two arm openings, wherein each are configured to receive the left or the right arm of the subject;

a fastener extending the length of the front of the functionalized garment in about the middle of the front of the functionalized garment;

a first top panel and a second top panel, wherein each top panel extends from the front of the functionalized garment to the back of the functionalized garment and are configured to form a left and a right shoulder and left upper chest and right upper chest portions of the functionalized garment and the two arm openings, wherein each top panel extends about one third of the length of the functionalized garment;

a first mesh insert and a second mesh insert, wherein the first mesh insert is attached to the first top panel and the fastener such that the first mesh insert is sandwiched between the first top panel and the fastener, wherein the second mesh insert is attached to the second top panel and the fastener such that the second mesh insert is sandwiched between the second top panel and the fastener;

a first mesh panel and a second mesh panel, wherein the first mesh panel extends laterally from the fastener around the right side of the functionalized garment to the back of the functionalized garment and extends laterally along the back of the functionalized garment and extends vertically to the top opening of the functionalized garment along the edge of the first top panel at a point that is less than half way across the back of the functionalized garment, wherein the second mesh panel extends laterally from the fastener around the left side of the functionalized garment to the back of the functionalized garment and extends laterally along the back of the functionalized garment and extends vertically to the top opening of the functionalized garment along the edge of the second top panel at a point that is less than half way across the back of the functionalized garment, wherein the first mesh panel is attached to the bottom portion of the first top panel and forms the bottom of the right arm opening, wherein the second mesh panel is attached to the bottom portion of the second top panel and forms the bottom of the left arm opening;

a compression panel, wherein the compression panel extends laterally away from the fastener along the bottom of the first and the second mesh panels, wherein the compression panel further extends around each side of the functionalized garment, wherein the compression panel further extends laterally across the back of the garment along the bottom of the first and the second mesh panels, wherein the compression panel further extends vertically up the middle of the back of the functionalized garment to the top opening between the first and the second mesh panels, wherein the compression panel comprises a sleeve at the bottom of the back portion of the compression panel;

an adjustable compression band, wherein the adjustable compression band is coupled to the compression panel, wherein the compression band has a first and a second end that are positioned in middle of the front of the garment and extend beyond the fastener, wherein the first and second ends are configured to be pulled to adjust the compression provided by the band, wherein the first and second ends are configured to releasably couple to the outer side of the compression band before and/or after adjustment, wherein the compression band extends laterally around the back of the functionalized garment through the sleeve;

a bottom portion, wherein the bottom portion is attached to the bottom of the compression panel and extends the length of the compression panel, wherein the bottom portion forms the bottom opening when the fastener is in the closed configuration, a flexible sensor, flexible electrode, flexible interconnect, and combinations thereof, wherein the flexible sensor, flexible electrode, or flexible interconnect and combinations thereof are coupled to the functionalized garment, one or more hard electronic components, wherein the one or more hard electronic components are coupled to the functionalized garment, and wherein one or more hard electronic components are coupled to one or more of the flexible sensors, flexible electrodes, and/or flexible interconnects.

Aspect 2: The functionalized garment of aspect 1, wherein the first and the second top panel are each made of a jersey material.

Aspect 3: The functionalized garment of aspects 1 or 2, wherein the bottom portion is made of a jersey material.

Aspect 4: The functionalized garment in any one of aspects 1 to 3, wherein the fastener is a zipper.

Aspect 5: The functionalized garment in any one of aspects 1 to 4, wherein the sensor(s) and/or electrode(s) are configured to detect a biopotential of a subject during use.

Aspect 6: The functionalized garment in any one of aspects 1 to 5, wherein at least one of the one or more hard components is configured to transmit and/or receive a signal.

Aspect 7: The functionalized garment in any one of aspects 1 to 6, wherein one or both of the top panels contain one or more pockets on the inner side of the functionalized garment.

Aspect 8: The functionalized garment in any one of aspects 1 to 7, wherein the first panel is attached to the first mesh insert by a conductive seam, the first panel is attached to the fastener by a conductive seam, or a combination thereof.

Aspect 9: The functionalized garment in any one of aspects 1 to 8, wherein the first panel is attached to the first mesh insert by a conductive seam, the first panel is attached to the fastener by a conductive seam, or a combination thereof; and the second panel is attached to the second mesh insert by a conductive seam, the second panel is attached to the fastener by a conductive seam, or a combination thereof Aspect 10: The functionalized garment of aspects 8 or 9, wherein the conductive seam comprises a hollow fabric with one or more wires.

Aspect 11: The functionalized garment of aspects 8 or 9, wherein the conductive seam comprises conductive yarn or threads.

Aspect 12: The functionalized garment of aspects 8 or 9, wherein the conductive seam comprises a thin-film, fabric, or bias tape with patterned ink-based interconnects.

Aspect 13: The functionalized garment of aspects 8 or 9, wherein the conductive seam comprises a connection point for the hard electronic component.

Aspect 14: The functionalized garment of aspects 8 or 9, wherein the conductive seam comprises a connection point to a circuit board, radio board, or antenna.

Aspect 15: The functionalized garment in any one of aspects 1 to 14, wherein one or more hard electronic components are positioned in the first panel, second panel, or a combination thereof, and wherein one or more hard electronic components are coupled to one or more of the flexible sensors, flexible electrodes, and/or flexible interconnects.

Aspect 16: A functionalized garment comprising a panel for housing one or more hard electronic components, wherein the panel is attached to the garment by a conductive seam, wherein one or more hard electronic components are coupled to one or more of the flexible sensors, flexible electrodes, and/or flexible interconnects, wherein the hard electronic component is connected to a conductive seam in the garment, and wherein the conductive seam comprises a connection point to a circuit board, radio board, or antenna.

Aspect 17: The functionalized garment of aspect 16, wherein the conductive seam comprises a hollow tube for housing one or more wires.

Aspect 18: The functionalized garment of aspect 16, wherein the conductive seam comprises conductive yarn or threads.

Aspect 19: The functionalized garment of aspect 16, wherein the conductive seam comprises a flexible interconnect comprising: a first thermoplastic polymer film; a first hole, where the first hole in in the first thermoplastic polymer film; a second thermoplastic polymer film; a second hole, where the second hole is in the second thermoplastic polymer film; a conductive trace; a first conductive pad, where the first conductive pad is electrically coupled to the conductive trace and where the first conductive pad is in physical contact with the first hole; and a second conductive pad, where the second conductive pad is electrically coupled to the conductive trace and where the second conductive pad is in physical contact with the second hole, where the conductive trace, the first conductive pad, and the second conductive pad are encapsulated between the first thermoplastic polymer film and the second thermoplastic polymer film.

Aspect 20: A method comprising:
applying the functionalized garment in any one of aspects 1 to 19 to a torso of a subject; and
detecting and/or measuring a biopotential of the subject.

Aspect 21: The method of aspect 20, further comprising transmitting a signal from one or more hard electrical components to a receiver that is external to the functionalized garment.

EXAMPLES

Now having described the embodiments of the present disclosure, in general, the following Examples describe some additional embodiments of the present disclosure. While embodiments of the present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure. The following examples are put forth so as to provide those of ordinary skill in the art with a complete disclosure and description of how to perform the methods and use the probes disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Example 1

Figure 6:
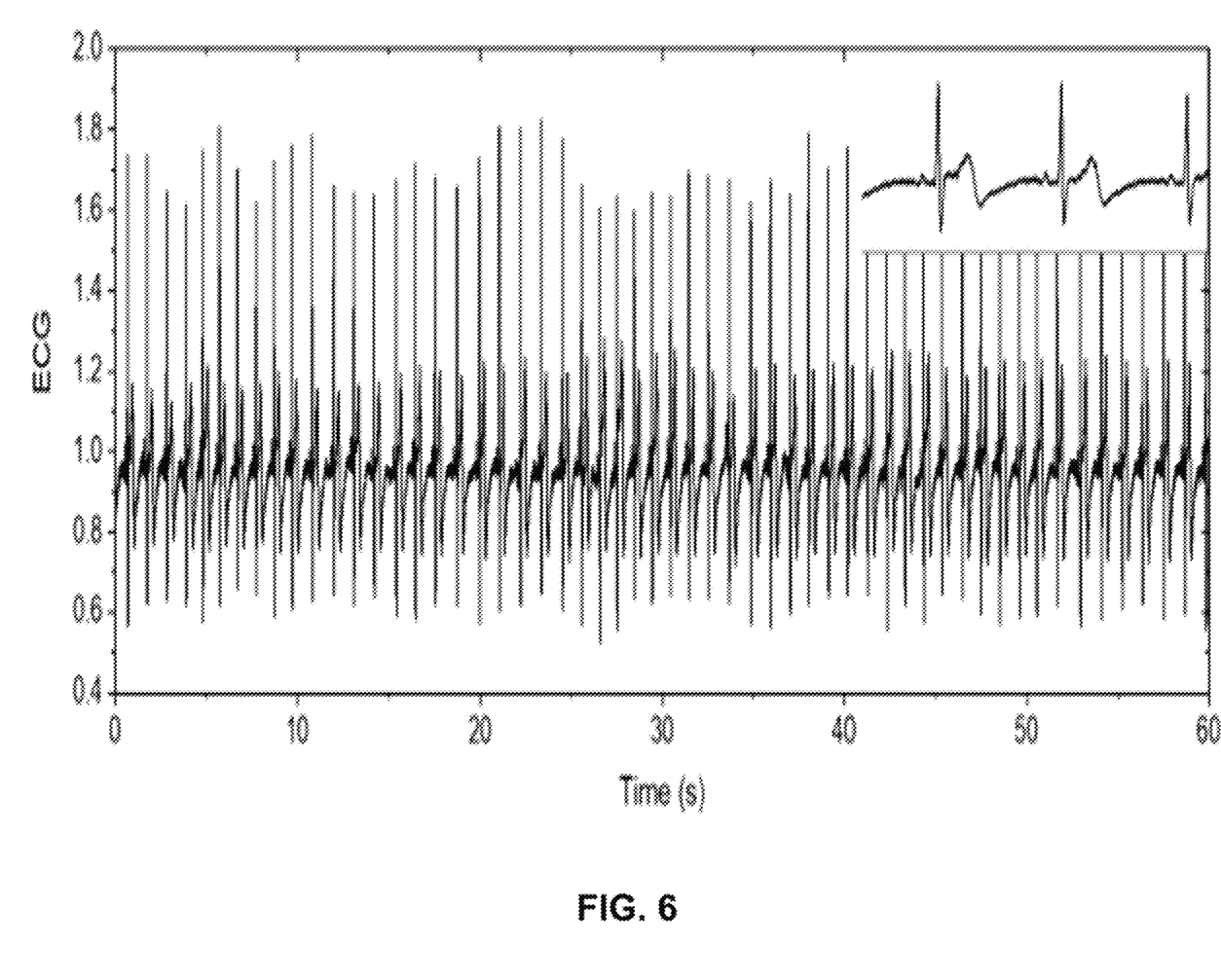
FIG. 6 shows ECG data generated from a 3 lead ECG shirt @ 120 Hz measurement frequency.

FIG. 6 shows ECG data generated from a 3 lead ECG shirt @ 120 Hz measurement frequency.

We claim:

1. A functionalized garment configured to encompass the torso of a subject, the functionalized garment comprising:
an upper opening configured to allow the passage of the head and neck of the subject
a bottom opening,
two arm openings, wherein each are configured to receive the left or the right arm of the subject;
a fastener extending the length of the front of the functionalized garment in about the middle of the front of the functionalized garment;
a first top panel and a second top panel, wherein each top panel extends from the front of the functionalized garment to the back of the functionalized garment and are configured to form a left and a right shoulder and left upper chest and right upper chest portions of the functionalized garment and the two arm openings, wherein each top panel extends about one third of the length of the functionalized garment;
a first mesh insert and a second mesh insert, wherein the first mesh insert is attached to the first top panel and the fastener such that the first mesh insert is sandwiched between the first top panel and the fastener, wherein the second mesh insert is attached to the second top panel and the fastener such that the second mesh insert is sandwiched between the second top panel and the fastener;
a first mesh panel and a second mesh panel,
wherein the first mesh panel extends laterally from the fastener around the right side of the functionalized garment to the back of the functionalized garment and extends laterally along the back of the functionalized garment and extends vertically to the top opening of the functionalized garment along the edge of the first top panel at a point that is less than half way across the back of the functionalized garment, wherein the second mesh panel extends laterally from the fastener around the left side of the functionalized garment to the back of the functionalized garment and extends laterally along the back of the functionalized garment and extends vertically to the top opening of the functionalized garment along the edge of the second top panel at a point that is less than half way across the back of the functionalized garment, wherein the first mesh panel is attached to the bottom portion of the first top panel and forms the bottom of the right arm opening, wherein the second mesh panel is attached to the bottom portion of the second top panel and forms the bottom of the left arm opening;

a compression panel, wherein the compression panel extends laterally away from the fastener along the bottom of the first and the second mesh panels, wherein the compression panel further extends around each side of the functionalized garment, wherein the compression panel further extends laterally across the back of the garment along the bottom of the first and the second mesh panels, wherein the compression panel further extends vertically up the middle of the back of the functionalized garment to the top opening between the first and the second mesh panels, wherein the compression panel comprises a sleeve at the bottom of the back portion of the compression panel;

an adjustable compression band, wherein the adjustable compression band is coupled to the compression panel, wherein the compression band has a first and a second end that are positioned in middle of the front of the garment and extend beyond the fastener, wherein the first and second ends are configured to be pulled to adjust the compression provided by the band, wherein the first and second ends are configured to releasably couple to the outer side of the compression band before and/or after adjustment, wherein the compression band extends laterally around the back of the functionalized garment through the sleeve;

a bottom portion, wherein the bottom portion is attached to the bottom of the compression panel and extends the length of the compression panel, wherein the bottom portion forms the bottom opening when the fastener is in the closed configuration, a flexible sensor, flexible electrode, flexible interconnect, and combinations thereof, wherein the flexible sensor, flexible electrode, or flexible interconnect and combinations thereof are coupled to the functionalized garment, one or more hard electronic components, wherein the one or more hard electronic components are coupled to the functionalized garment, and wherein one or more hard electronic components are coupled to one or more of the flexible sensors, flexible electrodes, and/or flexible interconnects.

2. The functionalized garment of claim 1, wherein the first and the second top panel are each made of a jersey material.

3. The functionalized garment of claim 1, wherein the bottom portion is made of a jersey material.

4. The functionalized garment of claim 1, wherein the fastener is a zipper.

5. The functionalized garment of claim 1, wherein the sensor(s) and/or electrode(s) are configured to detect a biopotential of a subject during use.

6. The functionalized garment of claim 1, wherein at least one of the one or more hard components is configured to transmit and/or receive a signal.

7. The functionalized garment of claim 1, wherein one or both of the top panels contain one or more pockets on the inner side of the functionalized garment.

8. The functionalized garment of claim 1, wherein the first panel is attached to the first mesh insert by a conductive seam, the first panel is attached to the fastener by a conductive seam, or a combination thereof.

9. The functionalized garment of claim 1, wherein the first panel is attached to the first mesh insert by a conductive seam, the first panel is attached to the fastener by a conductive seam, or a combination thereof; and the second panel is attached to the second mesh insert by a conductive seam, the second panel is attached to the fastener by a conductive seam, or a combination thereof.

10. The functionalized garment of claim 8, wherein the conductive seam comprises a hollow fabric with one or more wires.

11. The functionalized garment of claim 8, wherein the conductive seam comprises conductive yarn or threads.

12. The functionalized garment of claim 8, wherein the conductive seam comprises a thin-film, fabric, or bias tape with patterned ink-based interconnects.

13. The functionalized garment of claim 8, wherein the conductive seam comprises a connection point for the hard electronic component.

14. The functionalized garment of claim 8, wherein the conductive seam comprises a connection point to a circuit board, radio board, or antenna.

15. The functionalized garment of claim 1, wherein one or more hard electronic components are positioned in the first panel, second panel, or a combination thereof, and wherein one or more hard electronic components are coupled to one or more of the flexible sensors, flexible electrodes, and/or flexible interconnects.

16. A method comprising:
applying the functionalized garment of claim 1 to a torso of a subject; and
detecting and/or measuring a biopotential of the subject.

17. The method of claim 16, further comprising transmitting a signal from one or more hard electrical components to a receiver that is external to the functionalized garment.

* * * * *